(12) United States Patent
Weesner et al.

(10) Patent No.: US 6,565,054 B2
(45) Date of Patent: May 20, 2003

(54) SYRINGE HOLDER ATTACHMENT FOR MEDICATION

(75) Inventors: Kathryn A. Weesner, San Antonio, TX (US); Steven C. Walker, Baldwin, MO (US); John M. Shepherd, San Antonio, TX (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/789,704

(22) Filed: Feb. 22, 2001

(65) Prior Publication Data

US 2001/0030271 A1 Oct. 18, 2001

Related U.S. Application Data

(60) Provisional application No. 60/183,773, filed on Feb. 22, 2000.

(51) Int. Cl.[7] .................................................. A47B 96/06
(52) U.S. Cl. .............................. 248/229.17; 248/230.8; 248/316.1
(58) Field of Search .................... 248/316.7, 229.17, 248/313, 230.8, 228.8, 316.1, 213.2, 312, 541; 220/735; 215/390; 222/538, 371; D9/434; 604/131, 151

(56) References Cited

U.S. PATENT DOCUMENTS

| 390,089 | A | * | 9/1888 | McClelland ................ 222/80 |
| 612,296 | A | * | 10/1898 | Woodward ................ 215/390 |
| 836,033 | A | * | 11/1906 | Handy ................ 248/229.17 |
| 2,755,054 | A | * | 7/1956 | Churella ................ 248/229.17 |
| 4,819,838 | A | * | 4/1989 | Hart, Jr. ................ 222/538 |
| 5,370,622 | A | | 12/1994 | Livingston et al. ......... 604/151 |
| D363,017 | S | * | 10/1995 | Noble ................ D8/394 |
| D363,211 | S | * | 10/1995 | Noble ................ D8/395 |
| 5,755,415 | A | | 5/1998 | Sorg ................ 248/213.2 |
| 5,855,307 | A | * | 1/1999 | Biddick et al. ............. 224/267 |
| 5,873,859 | A | | 2/1999 | Muntz ................ 604/207 |
| 6,102,258 | A | * | 8/2000 | Riley et al. ................ 222/538 |
| 6,269,985 | B1 | * | 8/2001 | Brody ................ 222/538 |

FOREIGN PATENT DOCUMENTS

| EP | 0 925 027 | 6/1999 |
| FR | 993.774 | 11/1951 |
| FR | 2 746 375 | 9/1997 |
| GB | 1 221 752 | 2/1971 |

\* cited by examiner

*Primary Examiner*—Anita King
*Assistant Examiner*—Gwendolyn Baxter
(74) *Attorney, Agent, or Firm*—Elizabeth Arwine

(57) ABSTRACT

The device is for attaching a syringe or other type of dispenser to a container containing pharmaceutical. The device preferably includes a rubber band and a syringe holder. The syringe holder preferably includes an attachment lip, a bracket, and a clamp. The attachment lip and bracket preferably frame the rubber band, which is used to hold the attachment lip against the container. The clamp preferably is used to engage and hold the syringe.

17 Claims, 3 Drawing Sheets

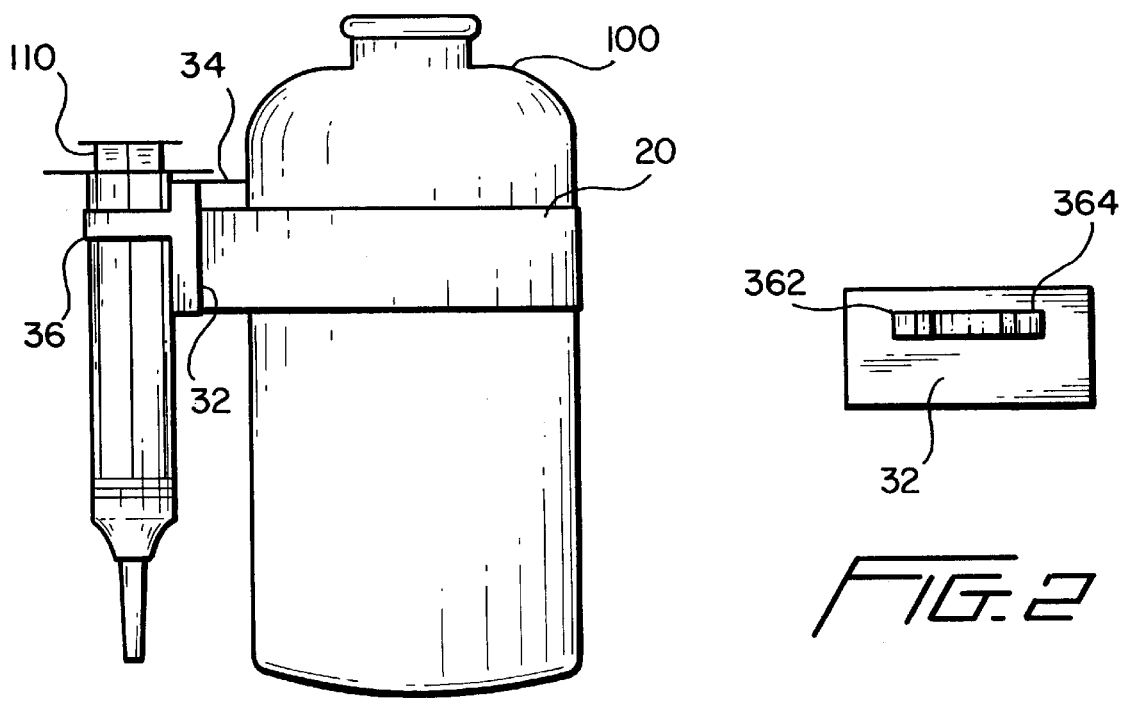
FIG. 1
FIG. 2
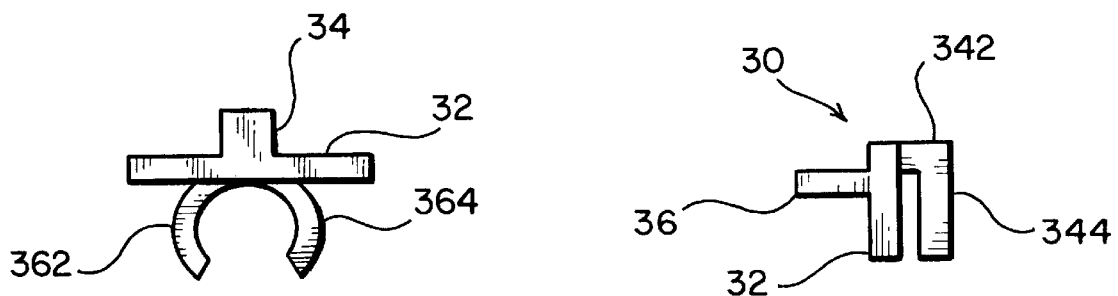
FIG. 3
FIG. 4

SYRINGE HOLDER ATTACHMENT FOR MEDICATION

This application claims the benefit of U.S. provisional Application Ser. No. 60/183,773, filed Feb. 22, 2000, which is hereby incorporated by reference.

I. FIELD OF THE INVENTION

The invention relates to an attachment for a prescription (or pharmaceutical) bottle to package it with a syringe or other medical dispensing device to keep the two items together. The invention preferably eliminates the need to search for the medical dispensing device to take/dispense medicine in addition to locating the medicine itself.

II. BACKGROUND OF THE INVENTION

Today there are many medicines and substances prescribed in liquid form that require oral administration via a syringe for proper dosing. In addition, there are a variety of one dose pharmaceuticals that are, for example, administrated in emergency situations such as on the battlefield or during an ambulance call. In certain other sittings sterility is not a concern and a syringe may be used repeatedly for administrating a particular pharmaceutical.

Presently when medicine is prescribed to a patient, either human or animal, that requires the use of a syringe for either oral or intravenous dosing, the syringe is provided as a separate piece from the bottle/vial containing the medicine. Usually for oral delivery, the syringe has a tip for drawing up the medicine from the bottle. The problem is that when the syringe is not attached to the bottle, the two items are easily separated and/or misplaced from one another, which then defeats the whole purpose of prescribing medication to a patient because the patient needs both items to take the pharmaceutical.

In the field when a medic, paramedic, or other emergency worker arrives to treat an injured and/or wounded person, the medic needs to have ready access to the instruments of his trade, which includes pharmaceutical bottles and syringes. Every second in an emergency situation can be precious and valuable to arrest further injury and/or harm to the patient; however, the medic will need to dig through his bag to locate three items, i.e., a medicine bottle (or other type of container), a syringe (or other type of medicine delivery system) of the appropriate size, and a needle. Depending on how big of a bag the medic is carrying and how well that bag is organized, the searching for these items will take time that potentially will have a detrimental impact on the likelihood of survival for the patient.

Notwithstanding the current situation for handling syringes and pharmaceutical bottles, a need exists for a better way.

III. SUMMARY OF THE INVENTION

The invention solves the above-discussed problems and obtains advantages not previously possible.

The invention preferably provides for a device for attaching a syringe to a bottle and includes a band and a syringe holder in communication with the band. The syringe holder preferably includes a bracket, a lip extending from the bracket, and a clamp extending from the bracket.

The invention preferably provides for a combination including a bottle, a dispenser, and an attachment device. The attachment device preferably includes a holder and a band in communication with the bottle. Preferably, the holder is in communication with the band and engages the dispenser. The holder preferably includes a bracket, a lip extending from the bracket, and a clamp preferably extending from the bracket and engaging the dispenser.

The invention provides a convenient and efficient way to store a disposable or reusable syringe used for the oral administration of liquid medicine or other substance during the time period for which the medicine/supplement is prescribed. Environments in which the invention may be used include on the battlefield, paramedic crews, home use, medical centers, or any other place where the convenience would be a benefit.

An object of the invention is to save time when locating a pharmaceutical bottle and a respective dispensing device, for example, in a medicine cabinet, refrigerator, or a medic's bag.

Another object of the invention is to reduce clutter by attaching the medical dispensing device to the pharmaceutical bottle.

Another object of the invention is to reduce the likelihood that the syringe will become separated from the pharmaceutical bottle.

An advantage obtained by the invention is a compact design that is easily attached to existing and future pharmaceutical bottles and other containers that contain medicine such as asthma medication.

Another advantage obtained by the invention is that the device is reusable.

A further advantage obtained by the invention is that the syringe is easily removed from the attachment for use, but will not fall out through normal, if not even rough, handling of the entire package.

Yet another advantage obtained by the invention is that it is easily scaled to fit different sizes of bottles and syringes.

Further features and advantages of the present invention, as well as the structure and operation of various embodiments of the present invention, are described in detail below with reference to the accompanying drawings. Given the following enabling description of the drawings, the apparatus and the method should become evident to a person of ordinary skill in the art.

IV. BRIEF DESCRIPTION OF THE DRAWINGS

The use of cross-hatching within these drawings should not be interpreted as a limitation on the potential materials used for construction. Like reference numerals in the figures represent and refer to the same element or function.

FIG. 1 illustrates a side view of a preferred embodiment of the invention attached to a bottle and a syringe.

FIG. 2 depicts a front view of the syringe holder of the preferred embodiment of the invention.

FIG. 3 illustrates a top view of the syringe holder of the preferred embodiment of the invention.

FIG. 4 depicts a side view of a syringe holder of the preferred embodiment of the invention.

V. DETAILED DESCRIPTION OF THE INVENTION

Figure 5:
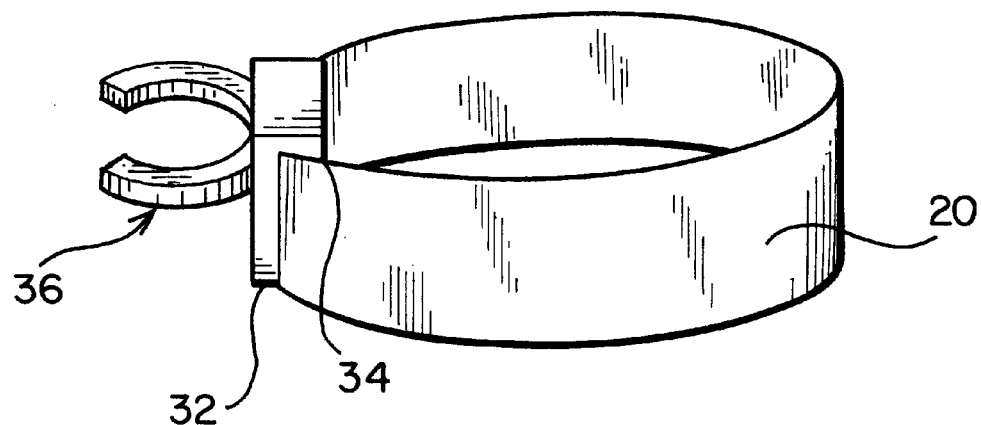
FIG. 5 illustrates a perspective view of an embodiment according to the invention.

FIGS. 1–4 illustrate the preferred embodiment of the invention. The invention is illustrated in FIG. 1 attached to a bottle 100 and a syringe with a plastic tip 110. The invention preferably includes a rubber band (or other type of elastic object) 20 and a syringe holder 30. The syringe holder 30 preferably includes a bracket 32, an attachment lip 34 extending from the backside (or posterior) of the bracket 32, and a clamp 36 extending from the front of the bracket 32 as shown, for example, in FIGS. 1 and 4.

The rubber band (or holding means) 20 preferably is an elastic material. In addition, the rubber band 20 preferably is taller than it is thick. The rubber band 20 preferably is placed around the pharmaceutical container such as a bottle. Preferably, the rubber band 20 has sufficient elasticity to encircle the container and hold the syringe holder 30 tightly against the container.

Referring to FIG. 4, the syringe holder (or attaching means) 30 preferably is molded plastic and a unitary piece. The attachment lip 34 preferably is a clip so that the rubber band 20 is inserted from the bottom of the lip 34. The attachment lip 34 preferably includes a horizontal wall 342 (or first member) extending from the posterior surface of the bracket 32 and a vertical wall 344 (or second member) extending down from the posterior edge of the horizontal wall 342. The horizontal wall 342 preferably is of sufficient depth to fit the rubber band 20 between the vertical wall 344 arid the bracket 32. The vertical wall 344 and the horizontal wall 342 preferably are of limited width to avoid curving the lip 34 to fit different sized pharmaceutical bottles. Also, the vertical wall 344 and the bracket 32 preferably run parallel to each other such that if one is curved in the longitudinal direction the other also is curved. The bracket 32 and the vertical wall 344 may be of different widths such that the bracket 32 is wider than the vertical wall 344 as illustrated in FIGS. 1, 3–4, and 6. However, the bracket 32 may be straight while the attachment lip 34 has a slight bottle fitting curvature as illustrated in FIG. 7.

The bracket 32 preferably is a planar piece that serves as the foundation upon which the attachment lip 34 and the clamp 36 are placed. The attachment lip 34 and the clamp 36 preferably extend from opposite sides (or surfaces) of the bracket 32. The bracket 32 and attachment lip 34 preferably frame the rubber band 20 on three sides in the region in which the rubber band 20 contacts the attachment lip 34 and bracket 32.

The clamp 36 preferably includes two annular members 362, 364 that extend from the bracket 32 in the same horizontal plane. The annular members 362, 364 will preferably be made of material that allows for a syringe to be inserted and removed multiple times. Preferably, the clamp 36 is fabricated to fit the intended syringe size, for example, 3, 5, or 10 cubic centimeter syringes with or without a needle (or straw or similar item). Preferably, the attached syringe will be sized to equal the prescribed dose. The annular members 362, 364 together preferably cover at least half of the circumference of the syringe. More preferably, the opening between the ends of the annular members 362, 364 will be such that the syringe is able to pass through it.

Figure 6:
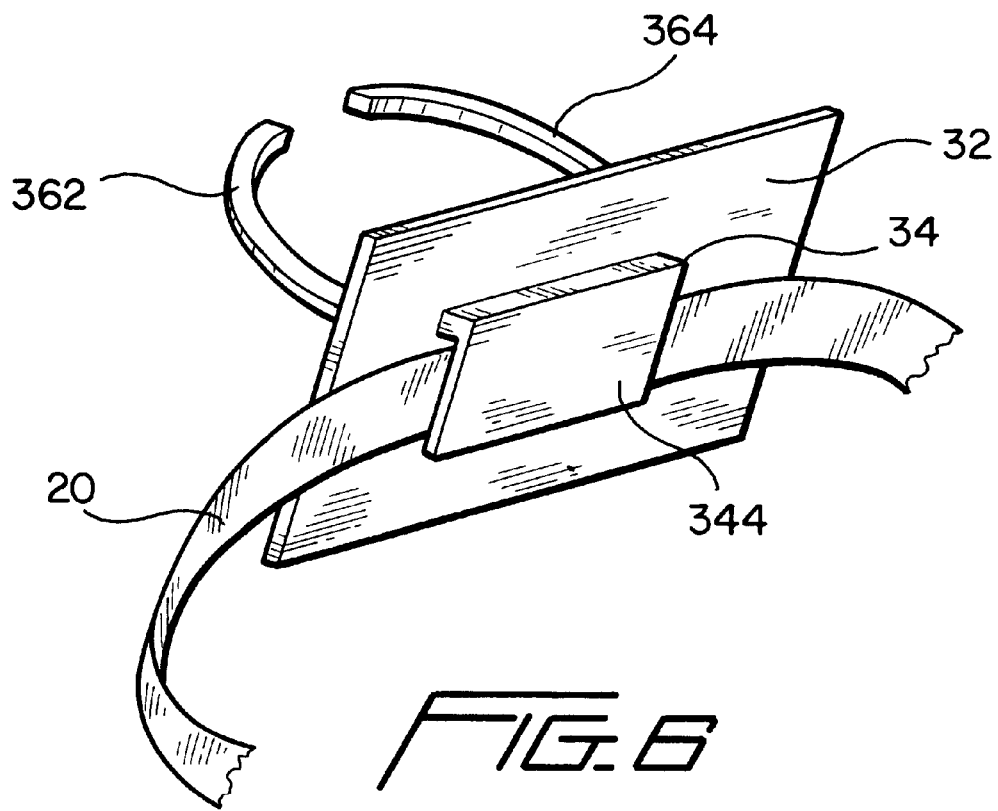
FIG. 6 depicts a perspective view of another embodiment according to the invention.
Figure 7:
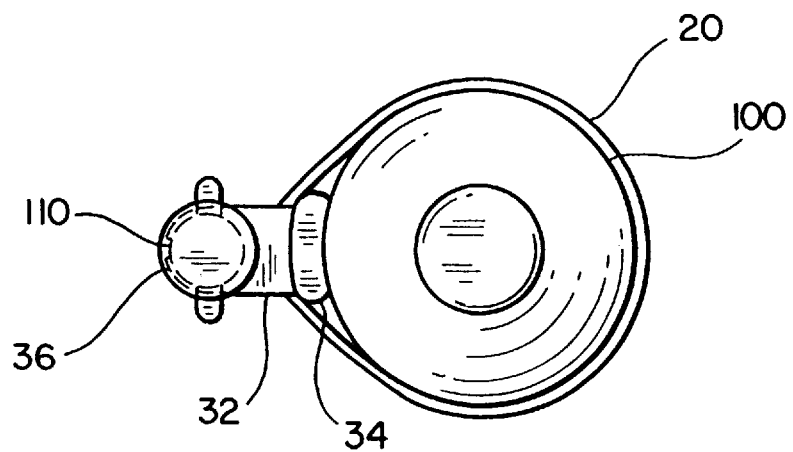
FIG. 7 illustrates a top view of another embodiment according to the invention.

FIGS. 5 and 6 illustrate an example of how the location of the clamp 36 and lip 34 may be at different heights on bracket 32. More particularly, the clamp 36 and lip 34 may be flush with the top of the bracket 32 or spaced down from the top.

Figure 8:
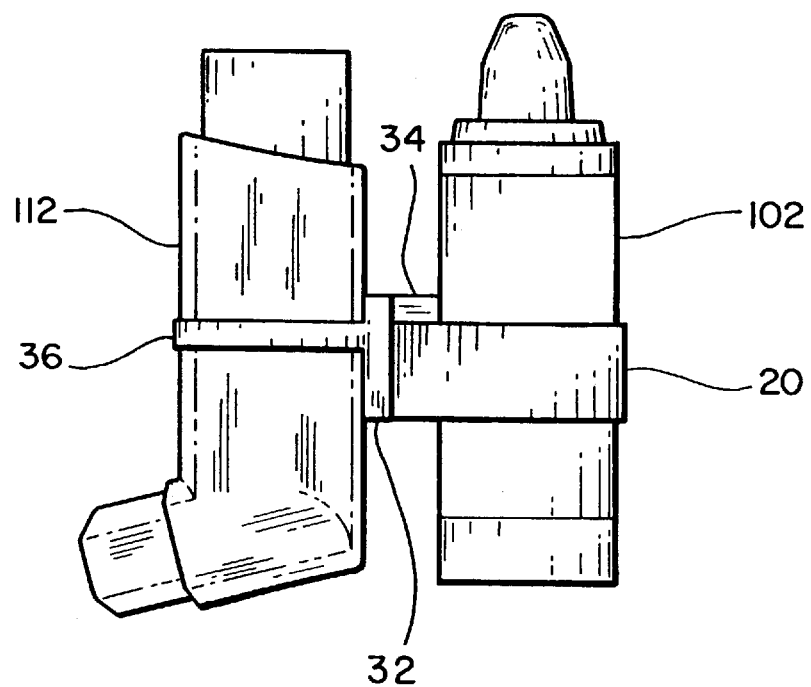
FIG. 8 depicts a side view of another embodiment according to the invention.

As illustrated in FIG. 8, a modification of the preferred embodiment is to change the size of the clamp 36 to secure a metered dose inhaler 112 such as that used to treat asthma. The rubber band 20 preferably then is of sufficient elasticity to secure the metered does inhaler 112 to a spacer tube 102 used to inhale the asthma medication from once the metered dose inhaler 112 dispenses it.

The device may be added to a pharmaceutical bottle at different levels of the distribution chain from the pharmaceutical company to the end purchaser/user of the pharmaceutical including a distributor or a pharmacy. The first preferred step of use is to loop the rubber band 20 around the pharmaceutical bottle preferably such that the horizontal wall 342 is above the rubber band 20. The second preferred step is to insert the syringe into the clamp 36. The third preferred step is to store the syringe with the pharmaceutical bottle such as in a medicine cabinet or a refrigerator. The fourth preferred step is to remove the bottle/syringe from the storage location. The fifth preferred step is to remove the syringe from the clamp 36. The sixth preferred step is to draw up the required medicine dose and to administrate the dose using the syringe. The seventh preferred step is to reattach the syringe into the clamp 36 for convenient storage until the next dosing.

Those skilled in the art will appreciate that various adaptations and modifications of the above-described devices and steps can be configured without departing from the scope and spirit of the their use in the method. Therefore, it is to be understood that, within the scope of the appended claims, the method may be practiced and arranged other than as specifically described herein.

We claim:

1. A device for attaching a syringe to a bottle comprising:
   a band, and
   a syringe holder in communication with said band, said syringe holder including
      a bracket;
      a lip extending from said bracket, said lip includes
         a first member extending from said bracket, and
         a second member extending from said first member; and
      a clamp extending from said bracket, said clamp includes two annular members extending from a side of said bracket opposite said lip; and
   wherein said band is partially framed by said bracket, said first member, and said second member.

2. The device according to claim 1, wherein said band includes an elastic material.

3. The device according to claim 1, wherein said first member is a horizontal wall.

4. The device according to claim 3, wherein said second member is a vertical wall.

5. The device according to claim 1, wherein said bracket is a vertical wall and said clamp is perpendicular to said bracket.

6. The device according to claim 1, wherein said clamp includes two annular members extending in a horizontal plane from a side of said bracket opposite said lip.

7. A method for using the device according to claim 1 comprising:
   securing the band to a bottle, and
   attaching a syringe to the clamp.

8. A device for attaching a syringe to a bottle comprising:
   a band, and
   a syringe holder in communication with said band, said syringe holder including
      a bracket,
      a lip extending from said bracket, said lip includes
         a first member extending from said bracket, and
         a second member extending from said first member, and a clamp extending from said bracket; and wherein said band is partially framed by said bracket, said first member, and said second member, and said second member is a curved wall with sufficient curvature to abut the bottle.

9. A combination comprising:

a container, a dispenser, and an attachment device including
- a band in communication with said container, said band includes an elastic material, and
- a holder in communication with said band and engaging said dispenser, said holder including
  - a bracket,
  - a lip extending from said bracket, said lip having
    - a first surface against said container, and
    - a second surface opposing said first surface contacting said band, and
  - a clamp extending from said bracket and engaging said dispenser; and wherein said band holds said lip against said container.

10. A combination comprising:

a container, a dispenser, and an attachment device including
- a band in communication with said container, said band includes an elastic material, and
- a holder in communication with said band and engaging said dispenser, said holder including
  - a bracket,
  - a lip extending from said bracket, said lip includes
    - a first member extending from said bracket, and
    - a second member extending from said first member; and
  - a clamp extending from said bracket and engaging said dispenser; and wherein said band is partially framed by said bracket, said first member, and said second member.

11. The combination according to claim 10, wherein said dispenser includes a syringe.

12. The combination according to claim 10, wherein said container contains pharmaceuticals.

13. The combination according to claim 10, wherein said first member is a horizontal wall.

14. The combination according to claim 13, wherein said second member is a vertical wall.

15. The combination according to claim 10, wherein said clamp includes two annular members extending in a horizontal plane from a side of said bracket opposite said lip.

16. A combination comprising:

a container, a dispenser, and an attachment device including
- a band in communication with said container, and
- a holder in communication with said band and engaging said dispenser, said holder including
  - a bracket,
  - a lip extending from said bracket, said lip includes
    - a first member extending from said bracket, and
    - a second member extending from said first member, and
  - a clamp extending from said bracket and engaging said dispenser; and wherein said band is partially framed by said bracket, said first member, and said second member, and said second member is a curved wall with sufficient curvature to abut said container.

17. A combination comprising:

a inhaler, a spacer, and an attachment device including
- a band in communication with said spacer, and
- a holder in communication with said band and engaging said inhaler, said holder including
  - a bracket,
  - a lip extending from said bracket, and
  - a clamp extending from said bracket and engaging said inhaler.

* * * * *